United States Patent
Oroskar et al.

(10) Patent No.: US 8,471,052 B2
(45) Date of Patent: Jun. 25, 2013

(54) HIGH-YIELD PRODUCTION OF ORGANIC NITRILES

(75) Inventors: Anil Oroskar, Oak Brook, IL (US); Paul Roman Kurek, Barrington, IL (US); Asha Oroskar, Oak Brook, IL (US)

(73) Assignee: Orochem Technologies Inc., Naperville, IL (US)

( * ) Notice: Subject to any disclaimer, the term of this patent is extended or adjusted under 35 U.S.C. 154(b) by 740 days.

(21) Appl. No.: 12/622,782

(22) Filed: Nov. 20, 2009

(65) Prior Publication Data

US 2011/0124901 A1    May 26, 2011

(51) Int. Cl.
*C07C 253/00* (2006.01)
(52) U.S. Cl.
USPC .......................................... 558/313; 558/311
(58) Field of Classification Search
USPC .................................... 558/311, 313
See application file for complete search history.

(56) References Cited

U.S. PATENT DOCUMENTS

| 3,725,457 A | 4/1973 | Borrel |
| 3,925,447 A | 12/1975 | Gelbein |
| 4,605,521 A * | 8/1986 | Eubanks et al. ............ 558/313 |

FOREIGN PATENT DOCUMENTS

EP    020663  A1    12/1986

\* cited by examiner

*Primary Examiner* — Joseph Kosack
(74) *Attorney, Agent, or Firm* — Richard P. Silverman & Assoc., LLC

(57) ABSTRACT

A process is disclosed for producing organic nitriles such as Acetonitrile or Hydrogen Cyanide, in which yields may exceed 90%, undesirable by-products are not produced, and handling of ammonia gas is avoided. In one aspect, a process includes preparing a feed including ammonium salts and water; introducing the feed into a reactor containing a catalyst; and heating the feed in the presence of the catalyst. The catalyst may advantageously include molybdenum on a silica or silica alumina support. The feed may be ammonium acetate in water with about 50 wt % ammonium acetate and the balance water or ammonium formate in water. In another aspect, a process includes preparing a feed including ammonium hydroxide and acetic acid; introducing the feed into a reactor containing a catalyst; and heating the feed in the presence of the catalyst.

2 Claims, No Drawings

HIGH-YIELD PRODUCTION OF ORGANIC NITRILES

FIELD OF THE DISCLOSURE

This disclosure relates to a process for producing organic nitriles, specifically Acetonitrile (ACN) and Hydrogen Cyanide (HCN) using a molybdenum/phosphorous-containing catalyst.

BACKGROUND OF THE DISCLOSURE

Organic nitriles such as Acetonitrile and Hydrogen Cyanide (HCN) are important building block in organic synthesis, and furthermore is used in the production of acrylic fibers and acrylonitrile-butadiene-styrene resins to make plastic moldings for a wide variety of applications. ACN is conventionally produced as a by-product from the acrylonitrile process, so that production trends for acetonitrile follow those of acrylonitrile. Recently this has led to a shortage of ACN.

A few methods for producing ACN as a direct product have been proposed. These processes require handling ammonia as a feed gas and have undesirable by-products.

U.S. Pat. No. 3,725,457 discloses the preparation of ACN by ammoxidation of acrolein, whereby increasing the amount of ammonia gas to this process results in a 2- to 10-fold yield increase. Yields of 42% ACN were reported.

U.S. Pat. No. 3,925,447 discloses preparation of hydrocarbon nitriles (but not ACN specifically) using ammonia gas and supported metal oxides having metal concentration in the range of 25 wt % to 75 wt %. According to this process, oxygen free conditions are required to produce nitriles with short contact times.

More recently, European patent publication EP0206632 (A1) has described attempts to prepare ACN using ammonia gas and ethanol over a molybdenum catalyst on a silica support. ACN was prepared by reaction of ethanol and ammonia in a 1:4 mole ratio at optimum temperatures of about 400° C. This process uses a 12-molybdophosphoric acid catalyst on a high surface area silica gel support; a surface area of 500 m$^2$/g is required to obtain the reported yield. The resulting product distribution gave 62% yield of acetonitrile with 4% unreacted ethanol, 12% ethylamine and 22%, 2-, and 4-picoline by-products formed through cracking side reactions.

There remains a need for a high-yield ACN production process that does not use acrylonitrile, avoids side reactions and by-products, and also avoids the dangers in handling ammonia gas.

SUMMARY OF THE DISCLOSURE

The present disclosure provides a process for producing acetonitrile in which yields may exceed 90%, undesirable by-products are not produced, and handling of ammonia gas is avoided.

According to an aspect of the disclosure, a process for producing ACN includes preparing a feed including ammonium acetate and water; introducing the feed into a reactor containing a catalyst; and heating the feed in the presence of the catalyst. The catalyst may advantageously include molybdenum on a silica or silica alumina support.

In specific examples, the feed is ammonium acetate in water, with about 50 wt % ammonium acetate and the balance water.

According to another aspect of the disclosure, a process for producing ACN includes preparing a feed including ammonium hydroxide and at least one of ethanol and acetic acid; introducing the feed into a reactor containing a catalyst; and heating the feed in the presence of the catalyst.

The process temperature is in the range of 100° C. to 700° C. In specific examples disclosed herein, the process temperature is in the range of 400° C. to about 600° C.

According to a further aspect of the disclosure, a process includes producing a mixture including ACN; and adding a salting agent to the mixture, thereby promoting a phase separation reaction in the mixture so that the ACN is concentrated in one phase. The salting agent may advantageously be ammonium acetate or sodium chloride. The phase separated ACN may then be recovered using a distillation process.

The foregoing has outlined, rather broadly, the preferred features of the present disclosure so that those skilled in the art may better understand the detailed description of the disclosure that follows. Additional features of the disclosure will be described hereinafter that form the subject of the claims of the disclosure. Those skilled in the art should appreciate that they can readily use the disclosed conception and specific embodiment as a basis for designing or modifying other structures for carrying out the same purposes of the present disclosure and that such other structures do not depart from the spirit and scope of the disclosure in its broadest form.

DETAILED DESCRIPTION

In accordance with the present disclosure, ACN may be produced with high yields using a molybdenum-containing catalyst, and using as reactants a combination of ethanol and ammonium hydroxide; a combination of ammonium hydroxide and acetic acid; or from ammonium acetate combined with water. These processes do not require handling ammonia gas.

In an embodiment of the process, the molybdenum-containing catalyst is prepared from 12-molybdenum phosphate ($H_3PMo_{12}O_{40}$) on a silica or silica alumina support. As discussed below, the catalyst support does not have stringent surface area requirements.

In addition, it has been found that the presence of water (i.e. presence and use of ammonium hydroxide) minimizes picoline formation, thus increasing yields of ACN to over 90% with only minimal by-product formation.

Furthermore, phase separation of ACN from bulk water in the reaction may be performed, lessening the heat utility of the process and making it more cost effective.

Details of the processes appear below in the discussion of the various examples. The reactants were fed into a tubular reactor, which may be prepared as detailed below, loaded with a molybdenum-containing catalyst. The reaction products were analyzed using a typical gas chromatography (GC) technique.

Preparation of Catalyst

A catalyst used in the disclosed processes may be prepared as follows:

Twenty grams of 12-phosphomolybdate (MoP) from Aesar Chemical are weighed out in a 250 ml glass beaker, then dissolved in 110 grams of DI water and stirred until a complete solution was obtained. A quantity of 100 grams of silica gel, having a 500 m$^2$/g surface area (e.g. D-50-60A microspheres), is weighed out into a 500 ml round bottom flask. The MoP solution is then poured all at once into the round bottom flask with swirling until all the silica is coated. (Water may be added if necessary to cover the silica.) The flask is placed on a rotoevaporator (a steaming cone may be used if available) and vacuum applied to 10 to 30 psig. Heating is then raised slowly, with stirring and rotating at a slow rate, until the water is removed and the silica becomes dry and free flowing; care should be taken to avoid pulling the dry silica out of the flask with vacuum. Rotation of the flask is continued after removal of the water, while the flask cools to room temperature. Vacuum is released after the flask cools. The silica should then contain about 20% MoP. Commercially available extrudates for this process contain 20 wt % 12-molybdophosphoric acid incorporated into a silica alumina dough.

The catalyst support as described above is formed from silica, but may also be formed from any of a variety of other materials. For example, the catalyst support may be formed from any of silica alumina, clays, pillard clays, kiesulghur, titanium, alumina, carbon, zeolites, water glass, barium, calcium inorganic salts, metal oxides, ceramic, functionalized supports, resins and mixtures of the same. The catalyst support may be made into any shape desired; for example, pellets, irregular particles, powders, spheres, extrudates, ceramic honeycomb, trilobe and pillared materials, and so forth. The catalyst may be loaded neat into the reactor, or inter-dispersed with inert packing material, trays, spacers, screens or the like.

It will be appreciated that catalysts may be formed of metals besides molybdenum; for example, transition metals in group IIIB-VIIIB, IB and IIB of the periodic table. Oxides of such metals may also be used to form the catalyst. Furthermore, metal compounds (including compounds of molybdenum) may be used with counter ions including (for example) phosphoric acid, fluorides, acetates, acetonylacetonates, chlorides, nitrates, sulfates, carbonates, bicarbonates and oxalates.

Construction and Operation of Reactor

A reactor suitable for carrying out a process according to the disclosure may be constructed as follows:

A vertical reactor tube (10 mm ID×150 mm length stainless steel column, having about 10 grams volume), with a 2 micron stainless steel frit, is loaded by pouring the dried catalyst into the tube, closed side down. (Alternatively, a tube 16 inches long×¾ inches ID with screens and quartz wool may be used.) The tube is vibrated so as to fill the tube evenly without voids. The tube is sealed with the frit and end fittings, and connected to reactor inlet and outlet line (e.g. ¼ inch tubing with swage-type fittings). The sealed tube is then placed into a furnace (typically a clamshell or muffle furnace).

The feedstock vessel is attached to a pump via an intake line. The pump is attached to a 4-way cross connector, to which is attached a nitrogen line, pressure gauge, knockout valve, back pressure regulator and pressure relief. A line leading from the cross connector connects to the reactor inlet. The reactor outlet connects to a glass dry ice condenser with a T/S 24/40 fitting which attaches to a round bottom flask with a side arm. This flask is placed into a Dewar of wet ice. The threaded side arm is connected and sealed to polypropylene tubing having a length of approximately 2 feet with a compressed O-ring. The other end of the tube is attached to an intermediate knock out pot. The exit line from this knock out pot is attached to an acidic scrubber inlet and exit line, then connected to a basic scrubber with the exit line from this scrubber open to the atmosphere for discharge.

The reaction is started by turning on $N_2$ gas or air and allowing it to pass through the reactor system. Heat is turned on to the furnace until a reaction temperature of 500° C. to 600° C. is reached. Alternatively, any catalyst deactivation can be reversed by regenerating the catalyst in air at a temperature between 500° C. and 600° C.

It will be appreciated that a reactor for carrying out the disclosed processes may be constructed in a variety of alternate ways. For example, the reactor may be a continuous tubular, upflow or downflow, batch, continuous batch, sequential step or staged processing type.

Identification of Process Reactants and Products by GC Analysis Conditions:
HP GC 5890 with thermal conductivity detector
24.1 ml/min He flow rate
30 meter Carbowax 20M, 1% coating, 0.32 mm ID capillary splitless
0.3 to 0.6 µl sample size
40° C. hold 1 min to 170° C. hold 1 min oven temperature at a ramp rate of 10° C./min.
Analysis time is 15 minutes
Injection port is at 250° C. isothermal
Detector at 250° C.
Elution details are shown below in Table 1.

TABLE 1

| Peak# | Compound | Elution Time (min) | Estimated b.p. ° C. |
|---|---|---|---|
| 1 | Air | 3.21-3.37 | 62 |
| 2 | NH3 as NH4OH | 3.8-5 | 74-80 |
| 3 | Ethylamine | 5.2-6.4 | 82-92 |
| 4 | Diethylamine | 6.62-7.1 | 96-100 |
| 5 | Ethanol | 7-7.4 | 105-110 |
| 6 | Acetonitrile | 7.7-8.5 | 113-115 |
| 7 | H2O | 8.7-8.9 | 120 |
| 8 | 2-Picoline | 11.21-11.70 | 142-144 |
| 9 | 4-Picoline | 12.6-12.9 | 156-158 |

EXAMPLE 1

Preparation of ACN from Ethanol and Ammonium Hydroxide

A feed vessel was charged with 350 grams of 30% ammonium hydroxide, and 46 grams of ethanol to give a 3:1 mole ratio. 4 grams of Tricat SH090416-2, 20/40 mesh were charged to a tubular reactor in a down-flow mode and run at autogenous pressure. The reactor was run as described above. The feed rate was 0.5 ml/min and temperature was 600° C. Analysis by GC showed 3.18% (normalized 65%) ACN and 1.7% (normalized 35%) diethylamine as the only products. Conversion of ethanol was 100%.

EXAMPLE 2

Preparation of ACN from Ammonium Acetate

To a feed vessel was blended 150 grams of ammonium acetate reagent. To this vessel was added 150 grams of water and the feed agitated until made homogeneous. The feed was set at a rate between 0.5 ml/min to 5 ml/min upflow. It will be appreciated, however, that a wide range of feed rates may be used to satisfy processing requirements in larger reactors; the feed rate may range from a few ml/min to gallons per minute. This feed was pumped into a reactor 16" long×¾" ID containing a catalyst prepared as described above. The catalyst generally comprises 12-molybdophosphoric acid impregnated on, or extruded with, silica or silica alumina oxides. 41 grams of this catalyst as extrudates were loaded into this reactor tube and placed inside a clamshell furnace. The furnace was heated to between 100° C. and 700° C. (with a preferred range of 400° C. to 600° C.) at 0.5 ml/min (preferred range of 0.5 ml/min to 5 ml/min) under autogenous pressure.

The product effluent that results is clear water white and may be condensed by any appropriate means such as a chiller, water, ice, dry ice, or cooling bath into a product receiver. Samples taken from this receiver are analyzed by GC as detailed above. The GC data shows that about 20% ACN is obtained without by-products; 2.5% total acetic acid and ammonia products are observed which may be recombined back into the starting feedstock. Accordingly, selectivities may approach 100%, with conversions of 97+% typically being realized, giving ACN in 97+ wt % yields. The ACN produced may be isolated by conventional means such as distillation or azeotropic distillation with water or other solvents such as benzene, hexanes, cyclohexane, and toluene and so forth.

The ACN produced may also be enriched by phase separation using a salt such as sodium chloride, sodium sulfate or the like. The preferred salt to separate ACN from bulk water is ammonium acetate as discussed below in Example 4.

Table 2 gives details of the reaction products using 50 wt % NH4OAc in water, with a processing temperature of 600° C., feed rates of 0.5 ml/min and 1 ml/min, and a catalyst prepared from 41 g extrudate from Tricat Industries, Inc.

TABLE 2

| Cut# | Weight of Cut Grams | % NH4OH | % ACN | % H2O | % HAc @ 11 min RT | Feed Rate (ml/min) |
|---|---|---|---|---|---|---|
| 1 L/O | 7.2 | 1.6 | 14.15 | 79.56 | 1.26 | 0.5 |
| 2 | 36.39 | 1.7 | 21.67 | 73.52 | 0.91 | 0.5 |
| 3 | 39.12 | 1.17 | 22.84 | 73.17 | 1.26 | 0.5 |
| 4 | 20.42 | 1.09 | 24.27 | 72.09 | 1.51 | 1 |
| 5 | 62.17 | 1.12 | 22.28 | 70.85 | 3.69 | 1 |
| 6 | 16.60 | 0.81 | 22.068 | 70.08 | 5.082 | 1 → 0.5 |
| 7 | 27.00 | 1.06 | 23.20 | 72.28 | 2.16 | 0.5 |
| Feedstock 150 gr NH4OAc + 150 gr H2O | 300 | 3.42 | 0 | 57.22 | 35.1 | — |

In this example, the total feed pumped was 232 g. The total product weight recovered was 208.9 g. Product recovery was thus 90%. No catalyst deactivation was observed.

This data indicates the successful use of concentrated feed, which improves the economics of the process.

No by-products were formed; however, it was observed that cracking or hydrolysis occurred to give NH4OH and HAc. It was also found that these hydrolysis products occur in the GC injection port at 250° C. Higher HAc formation was observed at higher flow rates.

EXAMPLE 3

Preparation of ACN from Ammonium Hydroxide and Acetic Acid

A feedstock was prepared by adding 350 grams of 30% ammonium hydroxide slowly to 120 grams of glacial acetic acid to give a 1.5:1 mole ratio of reactants. A feed rate was set at 0.5 ml/min upflow through the reactor described above. 3.25 grams of extruded 12-molybdo phosphoric acid with silica alumina was used as the catalyst. Reaction temperatures were in the range of 500° C. to 600° C. GC analysis of the product effluent, taken after 3 hours on stream, showed 14.4 wt % ACN formation (normalized to 94.7 wt %) and 0.8 wt % (normalized to 5.2 wt %) of an unknown product suspected as being diethylamine. No other products were observed, giving a 95% overall yield of ACN as a clear water white liquid product.

EXAMPLE 4

Salting out Acetonitrile—Ammonium Acetate and Sodium Chloride 10 grams of water were added to 5 grams of ACN; 1 gram of ammonium acetate was added and the mixture shaken for 30 seconds. Two phases resulted. Analysis of the upper phase shows that ACN can be recovered as the major product. The majority of the lower layer contains water with some ACN and salt. The upper layer is concentrated in ACN and can be further distilled, thereby minimizing utility requirements so that bulk water does not have to be heated to recover ACN typically as the water/ACN azeotrope.

This experiment was repeated using sodium chloride as salting agent. 10 grams of water was added to 10 grams of ACN; 1 gram of sodium chloride was added and the contents shaken for 30 seconds. Two layers again formed. Greater ACN recovery was obtained in the upper layer. However, from a process standpoint the use of ammonium acetate is preferred since it is also the feedstock; accordingly, no salt waste is generated.

Results show that both mixtures show a phase separation. Using NaCl gives a bigger layer and better recovery of ACN. Using NH4OAc also shows that ACN can be recovered with a little less ACN in the upper layer. However since the process uses NH4OAc it may be more cost effective to use this material as a phase separating agent. Some acetate is carried into the upper phase as well. However the use of sodium chloride is better to phase separate ACN then is ammonium acetate. The results of these experiments are summarized in Table 3.

TABLE 3

| Salting Agent | Layer | % CAN | % H2O | % HAc | Weight of layer (g) |
|---|---|---|---|---|---|
| NH4OAc | Upper | 74.4 | 24.1 | 1 | 1.32 |
| NH4OAc | Lower | 29.6 | 65.4 | 4.9 | 14.68 |
| NaCl | Upper | 76.9 | 21 | 0 | 6.59 |
| NaCl | Lower | 25.9 | 73.9 | 0 | 9.41 |

After the phase separation is performed, the ACN may be recovered using a distillation process such as azeotropic distillation, zone refining, freeze drying or a combination of such methods. Pure ACN may thus be recovered with minimal post treatment and without the need to process large volumes of water.

It will be appreciated that other salting agents may be used; for example, various salts of sodium, calcium, barium, potassium, magnesium, manganese, lithium and cesium. The salting agent may have any of a variety of counter ions; for example, chloride, acetate, sulfate, nitrate, fluoride, iodide, bicarbonate, carbonate and oxalate. Furthermore, a mixture of salting agents may be used.

The ACN production process disclosed herein provides improved yields while using simple to prepare catalysts without stringent surface area requirements. ACN can be produced with these catalysts using ethanol and ammonium hydroxide; ammonium hydroxide and acetic acid; or ammonium acetate and water, without the need for handling dangerous ammonia gas. In particular, the ammonium acetate process is environmentally friendly since little to no waste is generated.

While the disclosure has been described in terms of specific embodiments, it is evident in view of the foregoing description that numerous alternatives, modifications and variations will be apparent to those skilled in the art. For example, Hydrogen Cyanide can also be produced by this process with the use of Ammonium Formate solution or Formamide solution as the raw material. In-situ synthesis of Hydrogen Cyanide is desired in many chemical reactions in order to avoid large inventory of poisonous Hydrogen Cyanide. Accordingly, the disclosure is intended to encompass all such alternatives, modifications and variations which fall within the scope and spirit of the disclosure and the following claims.

We claim:

1. A process for producing acetonitrile (ACN), said process comprising:
   a. preparing a feed including ammonium acetate and water;
   b. introducing the feed into a reactor containing a catalyst comprising 12-molybdenum phosphate disposed on a support formed from silica or silica alumina;
   c. heating the feed to a temperature in the range of 100° C. to 700° C. in the presence of the catalyst to provide a reactor product mixture comprising ACN; and,
   d. recovering the ACN from the reactor product mixture using distillation.

2. The process of claim 1 further comprising adding a salting agent to the reactor product mixture prior to step (d) to promote a phase separation reaction in the reactor product mixture so that the ACN is concentrated in one phase, said salt comprising one or more of sodium, calcium, barium, potassium, magnesium, manganese, lithium, and cesium; and said salt including a counter ion being one or more of formate, chloride, acetate, sulfate, nitrate, fluoride, iodide, bicarbonate, carbonate and oxalate.

* * * * *